United States Patent
Ozawa et al.

(10) Patent No.: US 6,900,829 B1
(45) Date of Patent: *May 31, 2005

(54) ELECTRONIC ENDOSCOPE SYSTEM FOR REDUCING RANDOM NOISE OF A VIDEO SIGNAL

(75) Inventors: Ryo Ozawa, Tokyo (JP); Kouhei Iketani, Tokyo (JP)

(73) Assignee: PENTAX Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1146 days.

(21) Appl. No.: 08/829,187

(22) Filed: Mar. 31, 1997

(30) Foreign Application Priority Data

Apr. 3, 1996 (JP) .............................................. 8-106184

(51) Int. Cl.[7] .................................................. H04N 7/18
(52) U.S. Cl. ...................................................... 348/71
(58) Field of Search .............................. 348/65, 68, 70, 348/72, 76, 71; H04N 7/18

(56) References Cited

U.S. PATENT DOCUMENTS

| 5,031,036 A | * | 7/1991 | Kikuchi et al. | 348/71 |
| 5,408,263 A | * | 4/1995 | Kikuchi et al. | 348/68 |
| 5,475,420 A | * | 12/1995 | Buchin | 348/72 |

FOREIGN PATENT DOCUMENTS

| JP | 1181840 | 6/1989 |
| JP | 1212077 | 8/1989 |

* cited by examiner

*Primary Examiner*—Young Lee
(74) *Attorney, Agent, or Firm*—Greenblum & Bernstein, P.L.C.

(57) ABSTRACT

An electronic endoscope system which captures an image of an object and displays the same on a display device is provided with a noise reduction system. The noise reduction system reduces noise included in a frame of an image signal for each color component. The noise-reduced color components are stored in a buffer, and then output as a video signal to be transmitted to a display where a color image of the object is displayed.

11 Claims, 10 Drawing Sheets

ELECTRONIC ENDOSCOPE SYSTEM FOR REDUCING RANDOM NOISE OF A VIDEO SIGNAL

BACKGROUND OF THE INVENTION

The present invention relates to an electronic endoscope system to be used for displaying a color image of an object.

Generally, an electronic endoscope system is provided with an endoscope having a flexible tube accommodating an image sensor (such as a CCD) (Charge Coupled Device) and an objective lens at a distal end thereof. An image of an object is formed on an image receiving surface of the CCD by the objective lens system. The flexible tube also accommodates an optical fiber bundle. The distal end of the optical fiber bundle is located at the distal end of the flexible tube, and the proximal (operator-side) end of the optical fiber bundle is coupled to a light source unit to face to a light source included in the light source unit. Accordingly, light emitted by the light source is transmitted through the optical fiber bundle and illuminates the object.

The CCD includes a plurality of pixels. However, since the number of pixels for the CCD used in the endoscope is relatively small in comparison to CCDs used for camcorders or the like, in order to obtain a color image signal of the object, a color sequential method is used. Specifically, a rotary RGB color filter is provided between the optical fiber bundle and the light source inside the light source unit. By inserting each of an R (Red), G (Green) and B (Blue) filter sequentially into the optical path from the light source to the fiber bundle, red, green and blue light is sequentially transmitted through the fiber bundle to illuminate the object. Synchronously with a charge of the color illuminating the object, the CCD is driven to output an image signal. Accordingly, a red image signal (referred to as an R signal hereinafter), a green image signal (referred to as a G signal hereinafter), and a blue image signal (referred to as a B signal hereinafter) for one frame of an image to be displayed are sequentially output by the CCD. The R, G and B signals are processed, a video signal is created, and a color display is driven to display a color image. This process for obtaining the color image signals for one frame (or one field) sequentially, and for generating the color image based on each color image signal, is well known as a field sequential type color imaging process.

The R, G and B signals obtained as described above (i.e., in accordance with the field sequential type color imaging process) generally include random noise. For example, since the object is generally inside a human cavity, the object is illuminated only by the light emitted from the end surface of the fiber bundle, and thus, the amount of light which the CCD receives may vary greatly depending on the positioning of the distal end of the endoscope. Such a variation of the light amount may appear as noise and affect the displayed image. Further, other noise such as that due to dark current or the like may also affect the displayed image. If an observation is completed within a relatively short period noise may not be a large problem, however, if the observation continues for a relatively long period, noise may cause strain on the observer's eyes and an accurate diagnosis may not be made.

SUMMARY OF THE INVENTION

It is therefore an object of the invention to provide an improved electronic endoscope system in which random noise is effectively reduced.

According to the invention, there is provided an electronic endoscope system, comprising: an image capturing system, which receives a frame of an optical image and sequentially outputs a plurality of image signals respectively corresponding to a plurality of color components of the frame of the image; a noise reduction system, which reduces noise included in each of the plurality of image signals and outputs a plurality of noise-reduced image signals, respectively corresponding to the plurality of image signals; a memory which receives the plurality of noise-reduced image signals for each frame of the optical image; and a video signal generating system, which generates a video signal based on the noise-reduced image signals corresponding to the plurality of color components for each frame.

By reducing random noise, the noise reduction system allows the presentation of a clearer image of the object which allows a user of the endoscope to make a more accurate diagnosis.

Optionally, the video signal may include color component signals corresponding to the plurality of color components. For example, an Red, Green and Blue components may be included in the video signal. Alternatively, the video signal generating system may be configured to generate a composite signal.

Further, the plurality of color components may include components of three primary colors, e.g., R, G and B components.

Further optionally, the endoscope system may have a display device which receives the video signal and displays an image of the object.

Preferably, the image capturing system uses a field sequential color imaging process.

Optionally, the image capturing system comprising an image receiving element having a plurality of pixels, and wherein the noise reduction system reduces noise based on a previous image signal and a current image signal from corresponding pixels of the image receiving element.

In one preferred embodiment, the noise reduction system adds the previous image signal and the current image signal and then multiplies the sum by ½ to obtain the noise-reduced image signal.

Thus, the noise reduction system uses averaging to reduce the amount of noise in the output noise-reduced image signal.

Alternatively, the image capturing system comprising an image receiving element having a plurality of pixels, and wherein the noise reduction system reduces noise based on the noise-reduced image signal corresponding to a previously processed frame and a current image signal from corresponding pixels of the image receiving element.

Further optionally, the noise reduction system comprising a memory in which the noise-reduced image signal is temporarily stored.

Since a previously noise-reduced signal is fedback for use by the noise reduction system, the amount of noise reduction in the noise-reduced image signal may be even greater than that for the embodiment above.

Specifically, the noise reduction system generates the noise-reduced image signal in accordance with:

$$F'(n) = \alpha\{F(n) - F'(n-1)\} + F'(n-1),$$

wherein F'(n) is the noise-reduced image signal for an n-th pixel, F(n) is the current image signal for the n-th pixel, and α is a coefficient greater than zero and less than one.

Optionally, the coefficient α is different for each of the predetermined color components.

The use of the coefficient α allows a previous noise-reduced image signal to be proportionally averaged with the current image signal to more accurately reduced random noise while avoiding the danger of producing an incidental image, such as may occur if the coefficient α is set to low.

Further optionally, the predetermined color components consist of red, green and blue components, and wherein the coefficient α is the greatest when a corresponding color component is the green component and the coefficient α is smallest when a corresponding color component is the blue component.

Furthermore, the electronic endoscope system may be provided with a movement detector which outputs movement data representative of a moving amount of the object, and wherein the coefficient α is varied in accordance with the movement data.

Optionally, the coefficient α is greater when a value of the movement data is greater and the coefficient α is smaller when the value of the movement data is smaller.

The use of different values of the coefficient α for different color components takes into account the fact that the human eye is most sensitive to green light and least sensitive to blue light.

Further, the coefficient α changes stepwise with respect to a continuous change of the movement data.

Furthermore, the movement detector evaluates the moving amount of the object based on the current image signal and the noise-reduced image signal.

Still optionally, the image capturing system comprises a white light source, a plurality of color filters, a light transmitting member, and a CCD (Charge Coupled Device), wherein, in sequence and for a predetermined period of time, light emitted by the light source passes sequential through one of the plurality of color filters and is transmitted through the light transmitting member to illuminate the object, and wherein the plurality of color components correspond to the plurality of filters.

Alternatively, the plurality of colors includes three primary colors, wherein the noise reduction system comprises: a second memory for storing previously processed noise-reduced image signals respectively corresponding to the three primary color, separately; a first multiplier which multiples amplitude of the plurality of image signals corresponding to the three primary colors output by the image capturing system by coefficients α, β and γ, respectively, wherein 0<α<1, 0<β<1, and 0<γ<1; a second multiplier which reads and multiplies the noise-reduced image signals corresponding to the three primary colors and stored in the second memory by (1-α), (1-β) and (1-γ), respectively; an adder which adds the image signals corresponding to the three primary colors output from the first multiplier and the image signals output from the second multiplier, respectively, wherein the coefficients α, β and γ are determined in accordance with a sensitivity of human eyes, and wherein signals output by the adder are stored to the memory and the second memory as respective color component data.

DESCRIPTION OF THE EMBODIMENTS

Figure 1:
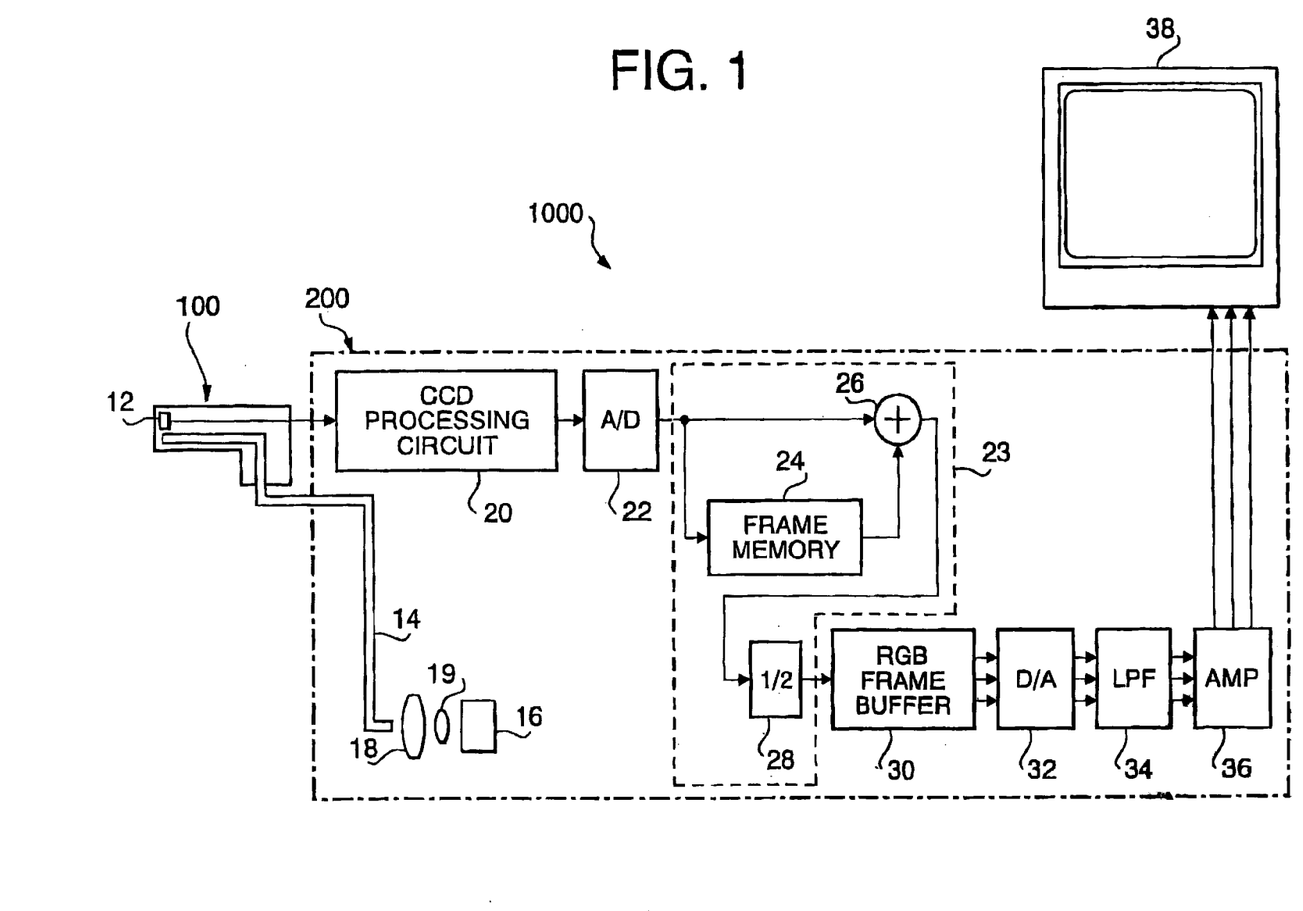
FIG. 1 is a block diagram of an endoscope according to a first embodiment of the invention.

FIG. 1 is a block diagram of an endoscope system 1000 according to a first embodiment of the invention. The endoscope system 1000 includes an endoscope unit 100, a light source unit 200 and a display 38. The endoscope unit 100 has, for example, a flexible tube accommodating a CCD 12 and an objective optical system (not shown) at a distal end of the endoscope unit 100. An image of an object is formed on the light receiving surface of the CCD 12 by the optical system. A light guide 14, such as an optical fiber bundle, runs from the light source unit 200 and then from a proximal (operator side) end of the endoscope unit 100 to the distal end of the endoscope unit 1000. In the light source unit 200, a proximal (operator-side) end of the light guide 14 faces a light source 16 through a converging lens 19 and a color filter disk 18. The light source emits a white light which includes light having various wavelengths, including red, green and blue components. The light emitted by the light source 16 is converged on the proximal (operator-side) end surface of the light guide 14 by the converging lens 19. The color filter disk 18 is rotated at a predetermined frequency corresponding to a display system for the display 38, for example, 25 Hz (which corresponds to the PAL system) or 30 Hz (which corresponds to the NTSC system). The color filter disk 18 is arranged such that as the color filter disk 18 rotates, the object is illuminated with R, G and B light, sequentially.

More particularly, the color filter disk 18 includes six evenly divided fan-shaped segments (not shown). Three of the segments are formed as light shielding segments (i.e., opaque), and the other three segments are red, green, and blue filtering segments, respectively.

As a particular numerical example, when the color filter disk 18 is rotated at 25 Hz, the disk rotates once in 40 ms. The object is illuminated with each color of light for 20/3 ms. That is, from the distal end surface of the light guide 14, the R light, G light and B light are emitted for 20/3 ms at every 40 ms to illuminate the object. Therefore, R, G and B images are formed on the light receiving surface of the CCD 12, sequentially during each period of 40 ms.

In this way, an optical image is formed on the light receiving surface of the CCD 12 and is converted into a frame of an analog signal during an illuminating period (20/3 msec), and the frame is then read out of the CCD 12 during the succeeding light shielding period (20/3 msec).

However, since the intensity of light passing through the color filters and the spectral sensitivity of the CCD 12 varies, the illuminating periods for each color light are slightly different from each other. The reading period, i.e., the period for reading the analog image signal, is always the same, i.e., the light shielding period.

The analog image signals are read using a well known CCD drive circuit (not shown). The analog signal for each color is processed by the CCD processing circuit 20, for example, gamma compensation or the like, and then converted into a digital image signal by an analog-to-digital (A/D) converter 22.

The digital image signal for each color is output from the A/D converter 22 to a noise reduction system 23. The noise reduction system 23 includes a frame memory 24, and adder 26, and a multiplier 28. In the noise reduction system 23, the digital image signal for each color is sampled synchronously with a clock pulse output by a timing generator (not shown) and stored in the frame memory 24.

Figure 2:
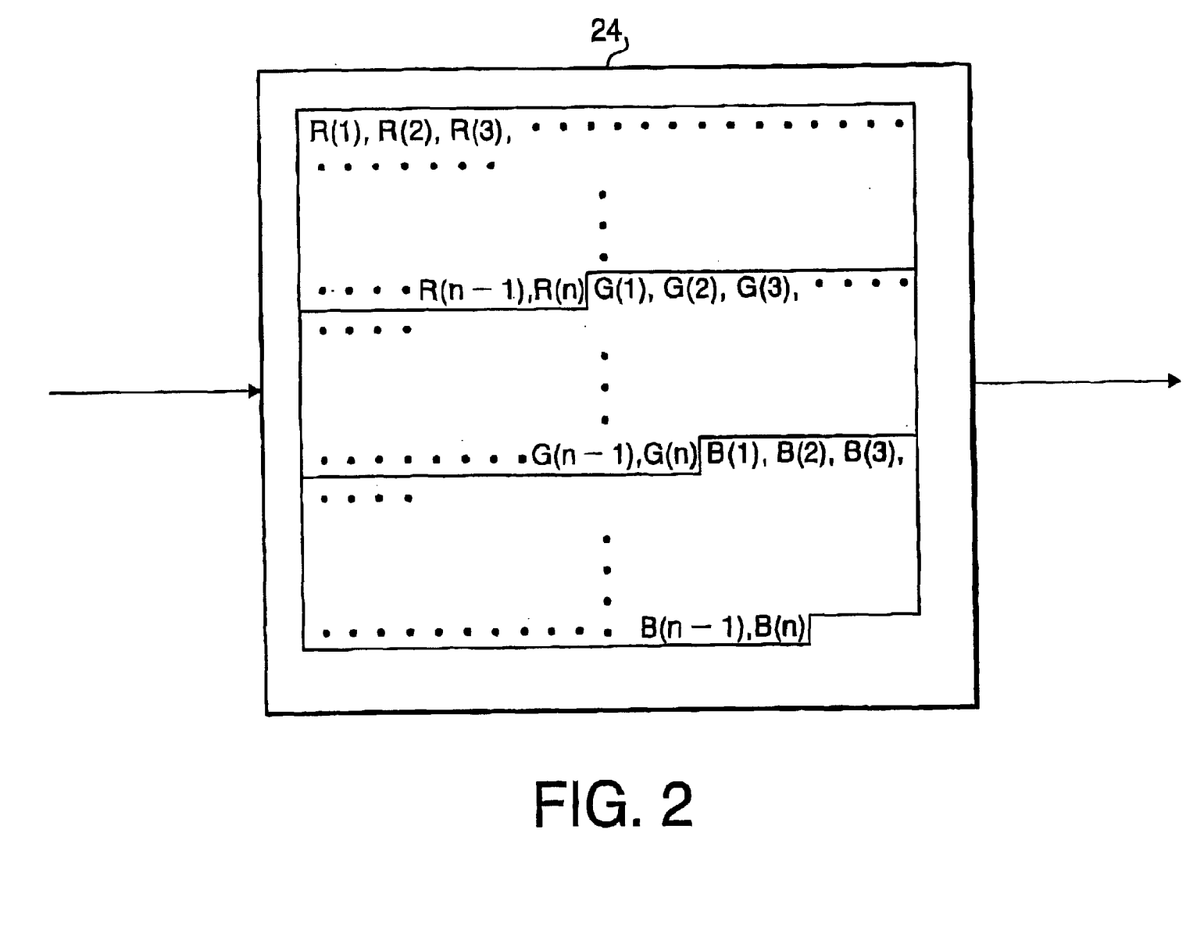
FIG. 2 shows a configuration of a frame memory of the endoscope.

As shown in FIG. 2, the frame memory 24 has capacity for three frames: a Red digital image signal R(1), R(2), ... , R(n); a Green digital image signal G(1), G(2), ... , G(n); and a Blue digital image signal B(1), B(2), ... , B(n), where n represents the total number of image pixels of a single frame. The digital image signal stored in each area of the frame memory 24 is updated synchronously with the rotation of the color filter disk 18. As the digital image signal stored in an area is updated, the previous digital image signal stored in the same area previously is read out and output to the adder 26 (see FIG. 1). For example, as an R digital image signal R(1), R(2), ... , R(n) is stored in the frame memory, the R digital image signal which was previously stored in the frame memory 24 is output to the adder 26.

It should be noted that the reading and writing of each digital image signal is processed on a basis of a horizontal scanning line. Therefore, a time difference between reading of an image signal corresponding to a pixel and writing of an image signal corresponding to the same pixel is equal to a period for processing an image signal for one horizontal scanning line. Accordingly, the previous digital image signal stored in the frame memory 24 can be read before the succeeding digital image signal corresponding to the same pixel is stored in the frame memory 24.

As shown in FIG. 1, the digital image signal output from the A/D converter 22 is also directly transmitted to the adder 26. Accordingly, the adder 26 adds, for each color, the digital image signal corresponding to the previous frame (previous digital image signal) and the digital image signal corresponding to the current frame (current digital image signal). The added digital image signal is input to the multiplier 28 and multiplied by a coefficient of ½ to average any random noise included in the previous digital image signal and the current digital image signal, such that, in the resultant noise-reduced digital image signal, the random noise is reduced.

Figure 3:
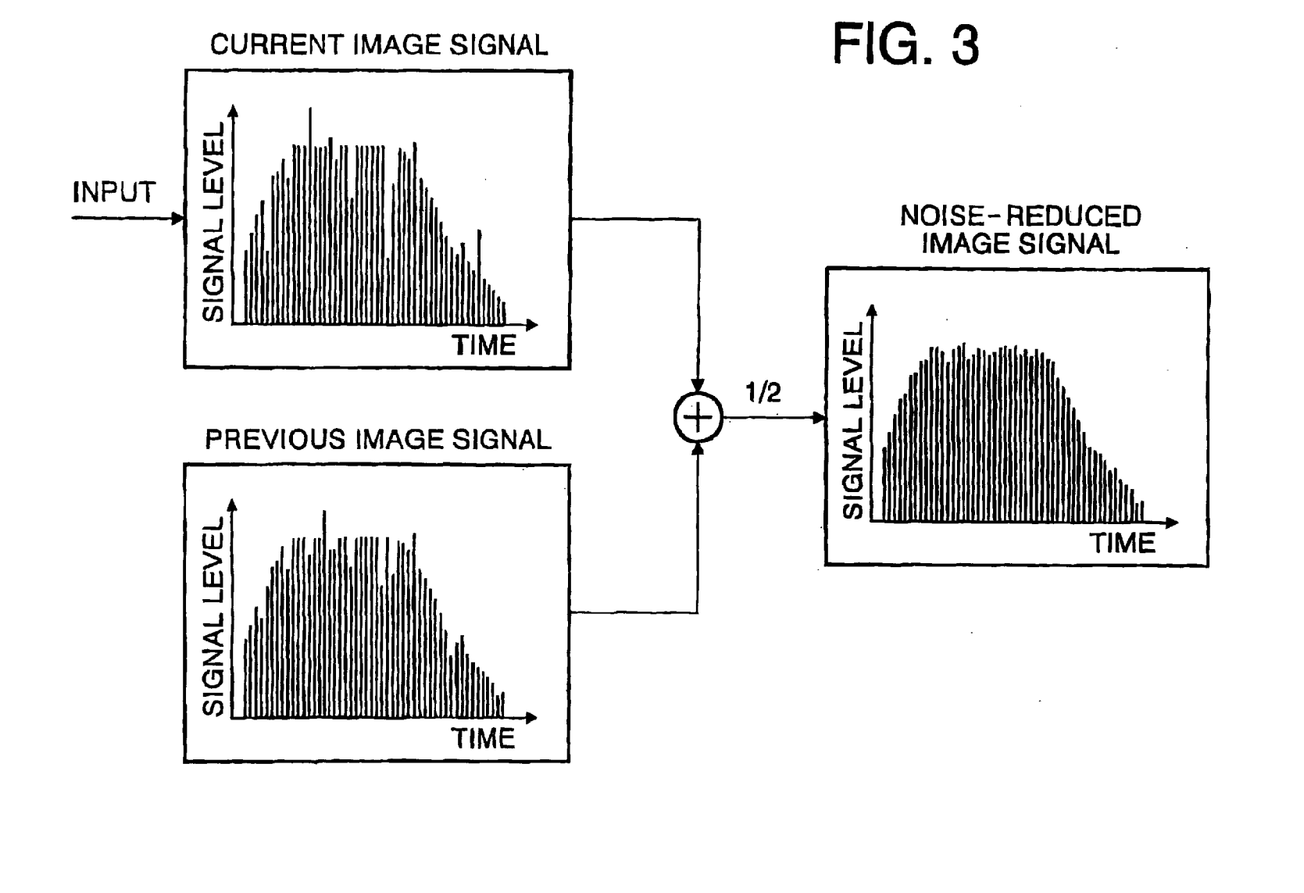
FIG. 3 shows frames of a digital image signal during processing according to the first embodiment.

FIG. 3 shows an example of random noise that may be included in the current digital image signal, the previous digital image signal, and the noise-reduced digital image signal.

Referring to FIG. 1, the noise-reduced digital image signal for each color is output from the multiplier 28 and temporarily stored in an RGB frame buffer 30. When the noise-reduced digital image signals corresponding to each color are all stored in the RGB frame buffer 30, the RGB frame buffer 30 outputs the noise-reduced digital image signals to be converted into analog image signals by a digital-to-analog (D/A) converter 32. The analog image signals are then transmitted to an amplifier 36 via a low pass filter (LPF) 34. The amplifier 36 amplifies the analog image signals and outputs the analog image signals corresponding to the three primary colors (R,G,B) to a display 38, such as a TV monitor or the like, such that a full color image is displayed on the display 38.

In order to display the full color image on the display 38, either an interlace scanning method, or a non-interlaced scanning method may be used. The reading order of the image signals stored in the RGB frame buffer 30 is determined depending on the scanning method used.

Figure 4:
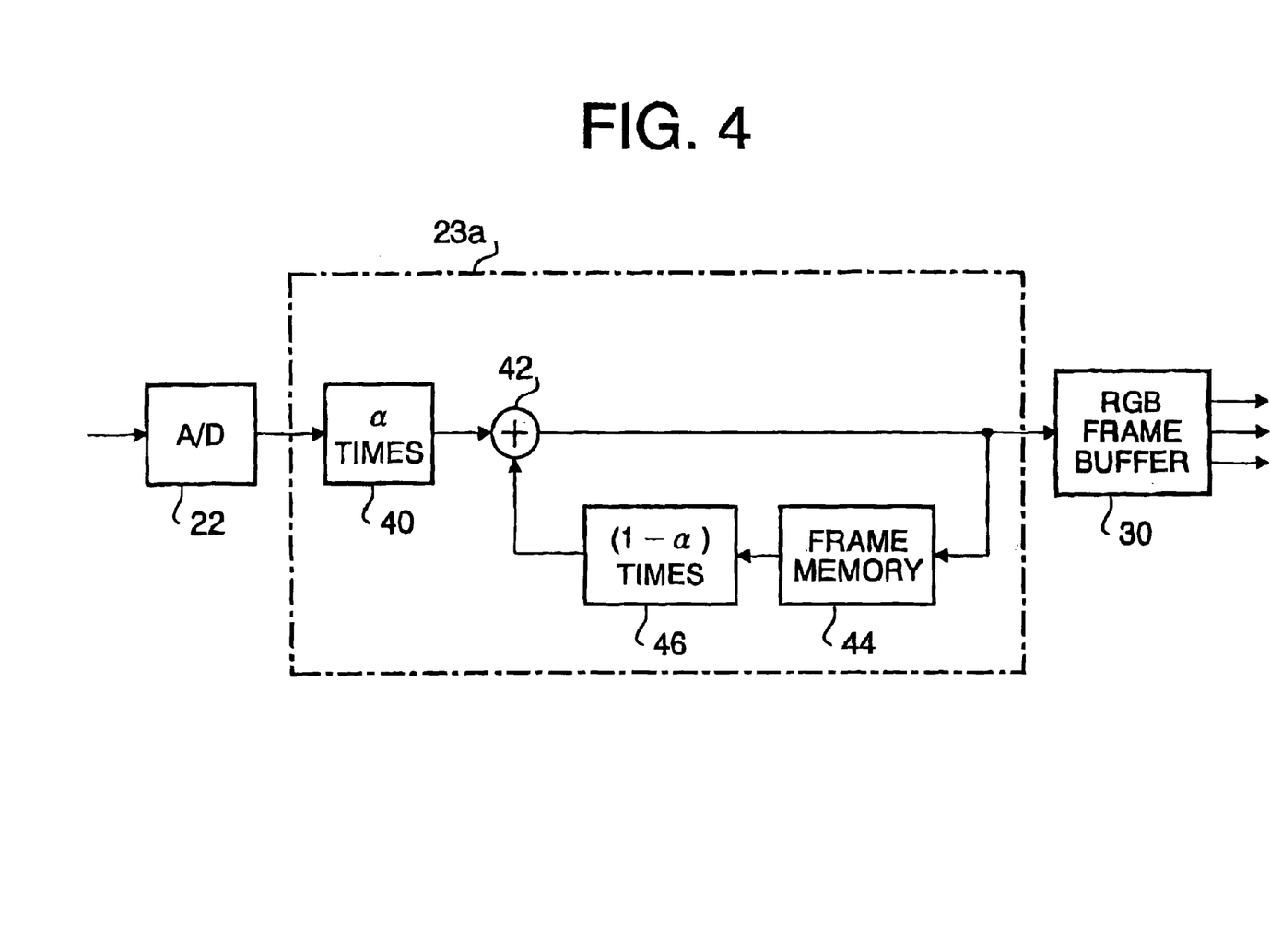
FIG. 4 is a block diagram of a noise reduction system according to a second embodiment.

FIG. 4 is a block diagram of a noise reduction system 23a according to a second embodiment. In the second embodiment, the noise reduction system 23a includes a first multiplier 40, an adder 42, a frame memory 44, and a second multiplier 46.

In general, the output of the A/D converter 22 is applied to the first multiplier 40 and the output of the multiplier 40 is applied to an adder 42. The output of the adder 42 is applied to both the RGB frame buffer 30 and the frame memory 44. The frame memory 44 outputs to the second multiplier 46 and the output of the second multiplier 46 is applied to the adder 42. Note that the structure of the frame memory 44 is substantially similar to that of the frame memory 24 of the first embodiment.

More specifically, the current digital image signal output from the A/D converter 22 is input to the first multiplier 40 where the current digital image signal is multiplied by a coefficient $\alpha(0<\alpha<1)$. The multiplied digital image signal is then applied to the adder 42. The adder 42 adds the multiplied digital image signal and a corresponding previous noise-reduced digital image signal (i.e., corresponding to a previous frame of the same color) that had been stored in the frame memory 44 and multiplied by $(1-\alpha)$ in a second multiplier 46. A noise-reduced digital image signal (i.e., having less random noise) is output from the adder 42 to both the frame memory 44 for feedback (as a previous noise-reduced digital image signal) and to the RGB frame buffer 30 for further processing.

Figure 5:
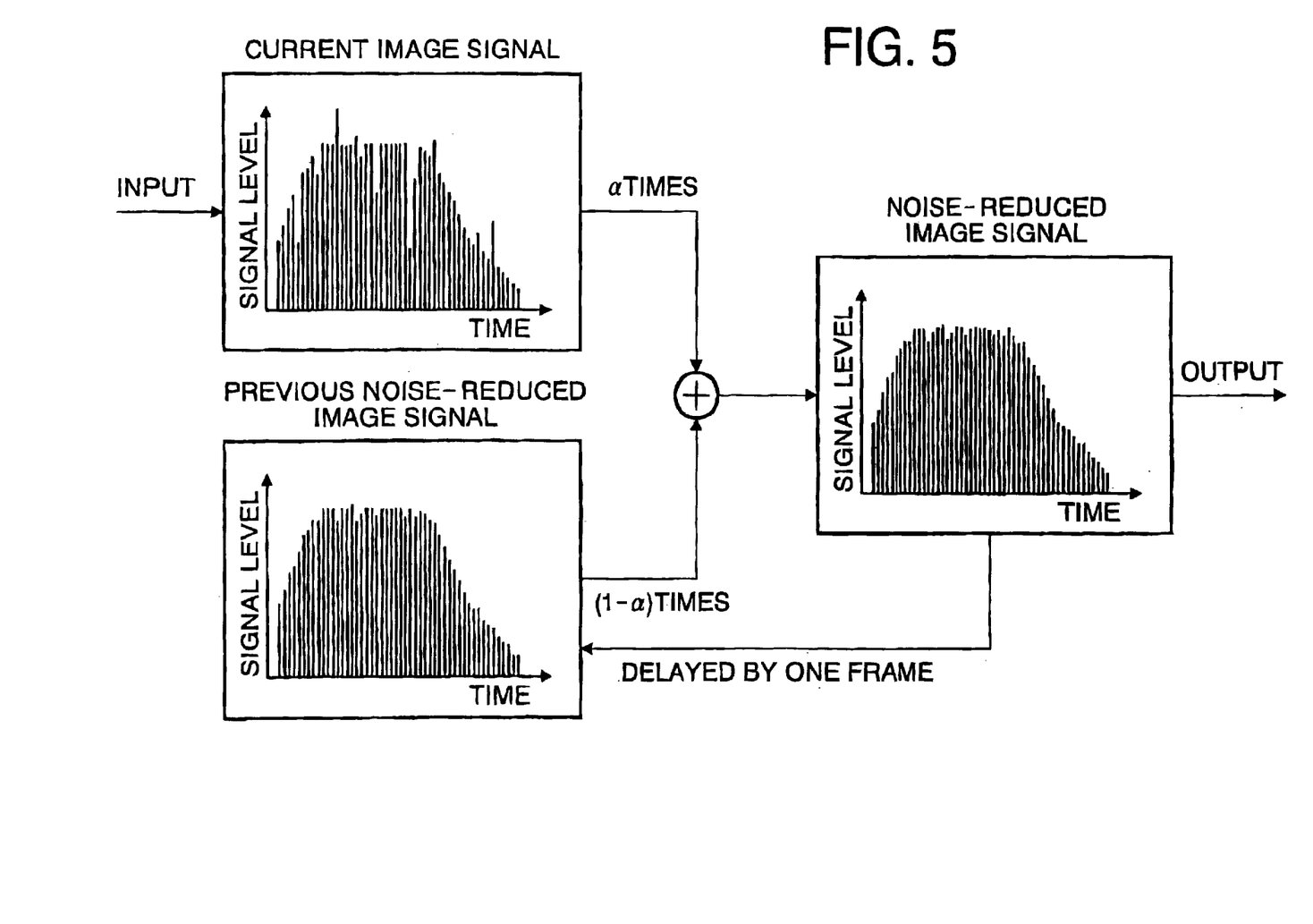
FIG. 5 shows frames of a digital image signal during processing according to the second embodiment.

FIG. 5 is similar to FIG. 3 and shows the related signals in accordance with the second embodiment.

A current digital image signal is multiplied by $\alpha$ and a previous noise-reduced digital image signal from the frame memory is multiplied by $(1-\alpha)$. The current digital image signal and the previous digital image signal are then added to obtain a resultant noise-reduced digital image signal in which random noise is reduced. The noise-reduced digital image signal is also stored in the frame memory 44 for use in subsequent image signal processing as a previous noise-reduced digital image signal.

Similarly to the first embodiment, the noise-reduced digital image signal is output from the adder 42 to the RGB frame buffer 30 and processed accordingly for display on the display 38.

According to the second embodiment, the noise-reduced digital image signal, which has been processed to reduce random noise, is fedback and used as a previous noise-reduced digital image signal such that there will be less random noise in the previous digital image signal used for adding in the second embodiment than in the previous digital image signal used for adding in the first embodiment. Accordingly, random noise can be reduced more effectively in the second embodiment than in the first embodiment.

In the second embodiment, by making the coefficient $\alpha$ smaller, an S/N (signal/noise) ratio of the digital image signal can be improved. However, if there is little co-relation between the previous noise-reduced digital image signal and the current digital image signal, e.g., when the object image has changed considerably, a smaller value of the coefficient α may generate an incidental image and worsen image quality. Therefore, the coefficient α is determined taking such a phenomenon into account.

Figure 6:
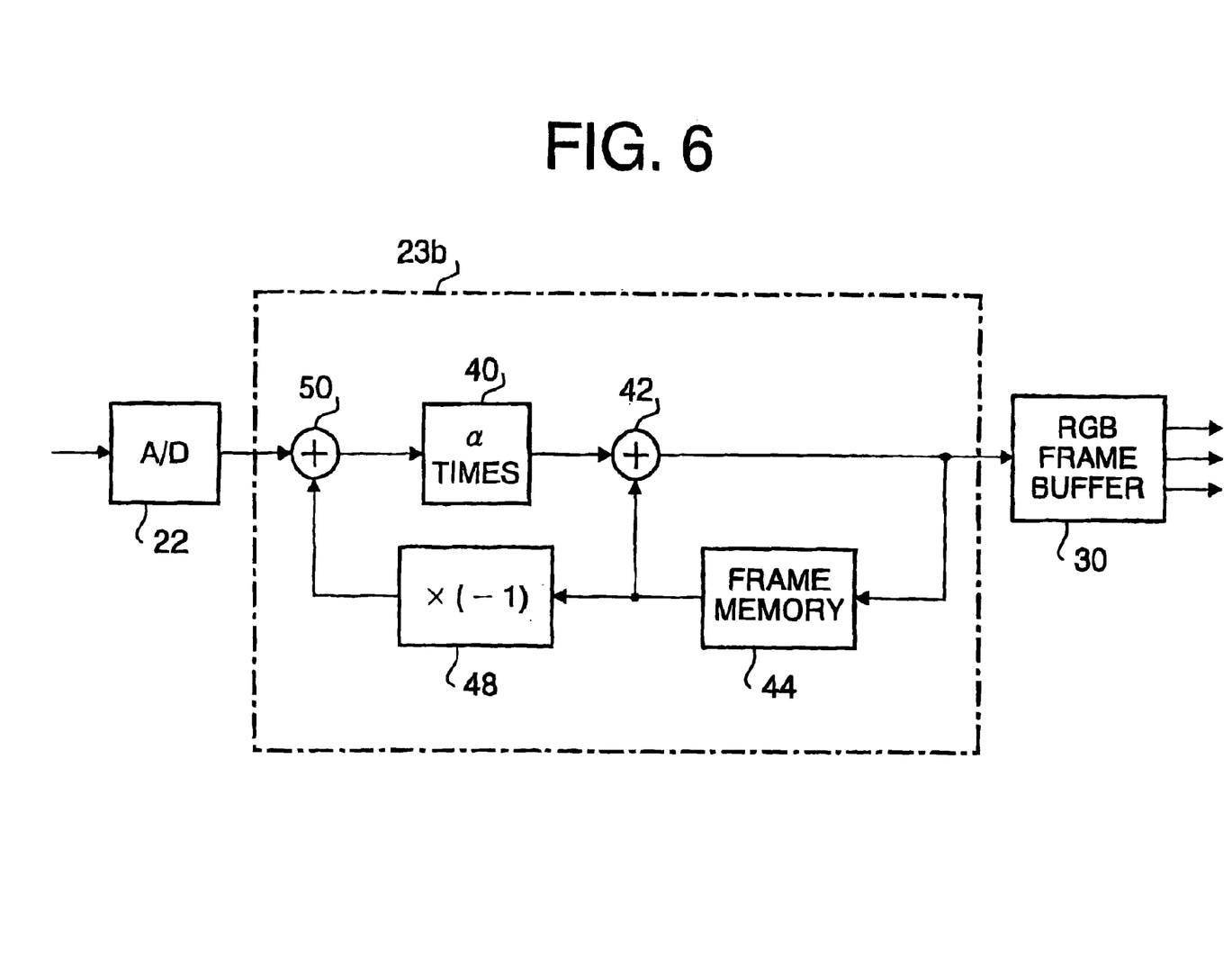
FIG. 6 is a block diagram of a noise reduction system according to a third embodiment.

FIG. 6 is a block diagram showing a noise reduction system 23b according to a third embodiment.

In this embodiment, the previous noise-reduced digital image signal is read out of the frame memory 44 and applied to both the adder 42 and a sign-reversing amplifier 48. The sign of the previous noise-reduced digital image signal is reversed by the sing reversing amplifier 48 and the sign reversed signal is applied to a second adder 50. The second adder 50 also receives the current digital image signal from the A/D converter 22. Therefore, the output of the second adder 50 represents the difference between the current digital image signal and the previous noise-reduced digital image signal for each color. The output of the second adder 50 is multiplied by the coefficient α in the first multiplier 40 and input to the adder 42. The adder 42 adds the previous noise-reduced digital image signal from the frame memory 44 and the output of the first multiplier 40 to produce a resultant noise-reduced digital image signal that is sent to the RGB frame buffer for further processing. The noise-reduced digital image signal is also stored in the frame memory 44 for use in subsequent image signal processing as a previous noise-reduced digital image signal.

As explained in the following, the noise-reduced digital image signal output by the adder 42 in FIG. 6 is functionally equivalent to the resultant digital image signal output by the adder 42 in FIG. 4.

In the noise reduction system 23a shown in FIG. 4, the following relationship is satisfied:

$$F'(n) = \alpha F(n) + (1-\alpha) F'(n-1) \tag{1}$$

where, F(n) represents the current digital image signal for the n-th pixel output from the A/D converter 22 and F'(n) represents the noise-reduced digital image signal for the n-th pixel output from the adder 42.

In the noise reduction system 23b shown in FIG. 6, the following relationship is satisfied:

$$F'(n) = \alpha(F(n) - F'(n-1)) + F'(n-1) \tag{2}$$

The equation (2) can also be obtained by modifying the equation (1). That is:

$$F'(n) = \alpha F(n) + F'(n-1) - \alpha F'(n-1) = \alpha F(n) - \alpha F'(n-1) + F'(n-1) = \alpha(F(n) - F'(n-1)) + F'(n-1)$$

Thus, the noise reduction system 23a, 23b shown in FIGS. 4 and 6 are functionally equivalent.

According to the structure shown in FIG. 4, the first multiplier 40 and the second multiplier 46 are necessary. In FIG. 6, only the first multiplier 40 is necessary. On the other hand, in FIG. 4, only the adder 42 is required, while, in FIG. 6, the adder 42 and the second adder 50 are necessary.

Generally, the circuit structure of a multiplier is more complicated than the structure of an adder or sign reversing amplifier. Therefore, the structure shown in FIG. 6 can be realized at a lower cost than the structure shown in FIG. 4.

Figure 7:
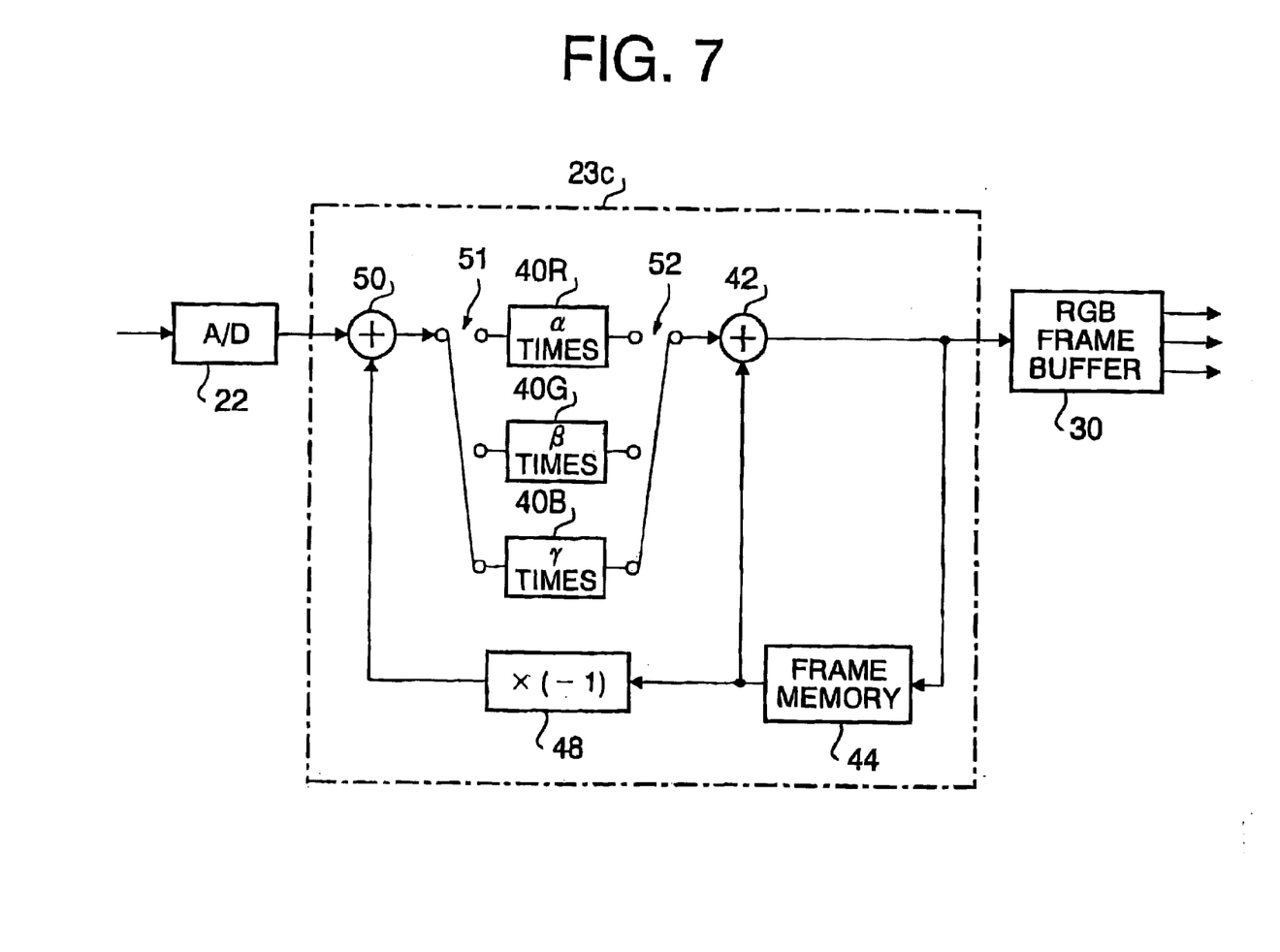
FIG. 7 is a block diagram of a noise reduction system according to a fourth embodiment.

FIG. 7 is a block diagram of a noise reduction system 23c according to a fourth embodiment of the invention. The noise reduction system 23c according to the fourth embodiment is essentially a modification of the noise reduction system 23b shown in FIG. 6.

In the fourth embodiment, as shown in FIG. 7, rather than providing the first multiplier 40 having the coefficient α between the second adder 50 and the adder 42, a group of three multipliers 40R, 40G, and 40B are provided (i.e., one for each color R,G, and B). The multipliers 40R, 40G and 40B use coefficients α(0<α<1), β(0<β<1) and γ(0<γ<1), respectively. Further, the noise reduction system 23b is provided with a switch 51, which selectively connects the multipliers 40R, 40G and 40B to the second adder 50, and a switch 52 which selectively connects the multipliers 40R, 40G and 40B to the adder 42.

When the current digital image signal is for a red image, the switches 51 and 52 are controlled to connect the multiplier 40R between the second adder 50 and the adder 42; when the current digital image signal is for a green image, the multiplier 40G is connected between the second adder 50 and the adder 42; and when the current digital image signal is for a blue image, the multiplier 40B is connected between the second adder 50 and the adder 42. In particular, the switches 51 and 52 are controlled in accordance with the clock pulse described above.

As is well known, among the three primary colors: red, green and blue, human eyes are most sensitive to green light and least sensitive to blue light. Thus, in the fourth embodiment, the coefficients α, β, and γ are set accordingly, that is, γ<α<β. According to the fourth embodiment, both random noise and deterioration of the image quality, for example, due to formation of an incidental image, are reduced for each color.

Figure 8:
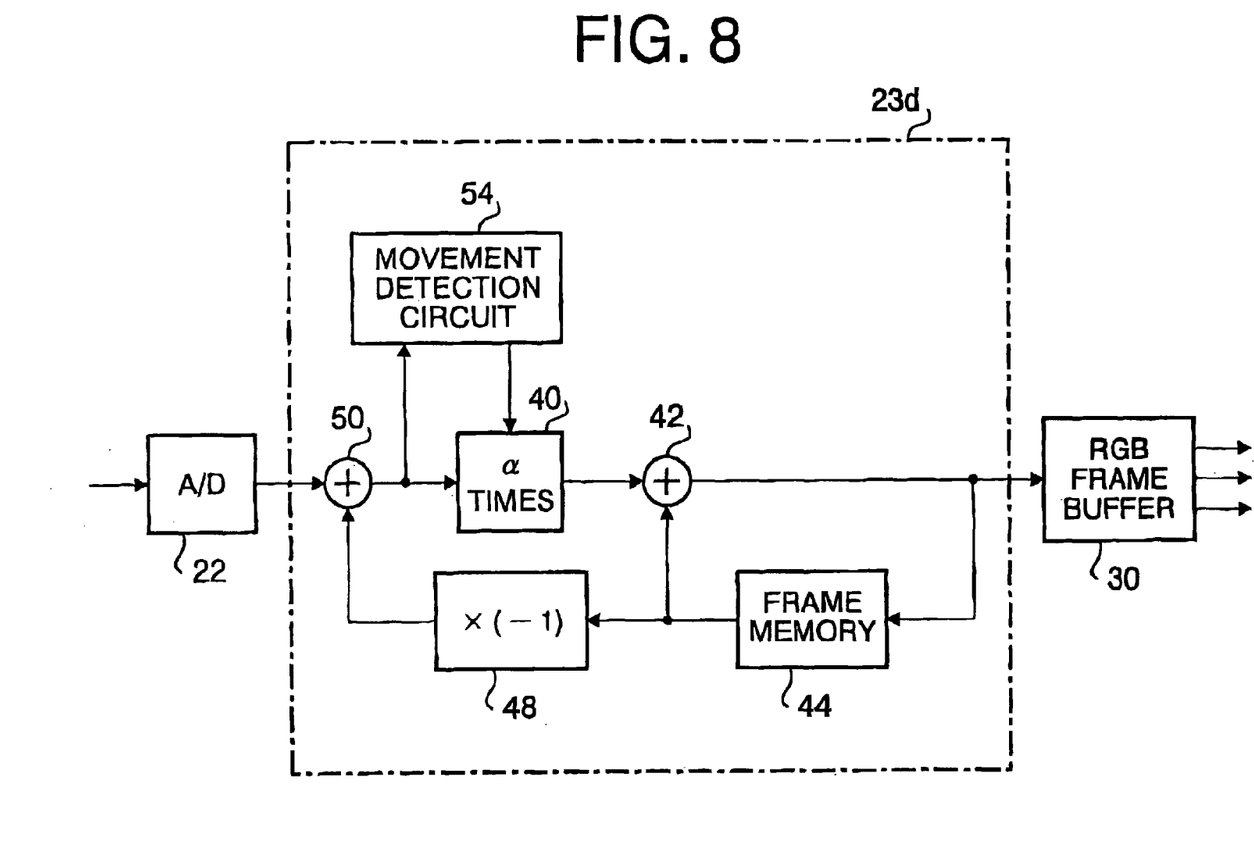
FIG. 8 is a block diagram of a noise reduction system according to a fifth embodiment.

FIG. 8 is a block diagram of a noise reduction system 23d according to a fifth embodiment. The noise reduction system 23d according to the fifth embodiment is essentially a modification of a noise reduction system 23b shown in FIG. 6. In particular, the noise reduction system 23d is provided with a movement detecting circuit 54 that receives the output of the second adder 50 and provides input to the first multiplier 40 such that the coefficient α is varied depending on the output of the movement detecting circuit 54.

The movement detecting circuit 54 evaluates the digital image signal output from the second adder 50 for each color to detect movement of the object. If the object does not move, or moves only a little, that is, the current digital image signal and the previous noise-reduced digital image signal are closely related to each other, the object image is treated as a still image. In such a case, the coefficient α is set to a relatively small value in order to reduced random noise as much as possible. On the other hand, if the object is moving, that is, the correlation between the current digital image signal and the previous noise-reduced digital image signal is not close, the coefficient α is set to a larger value in order to avoid production of an incidental image.

Figure 9:
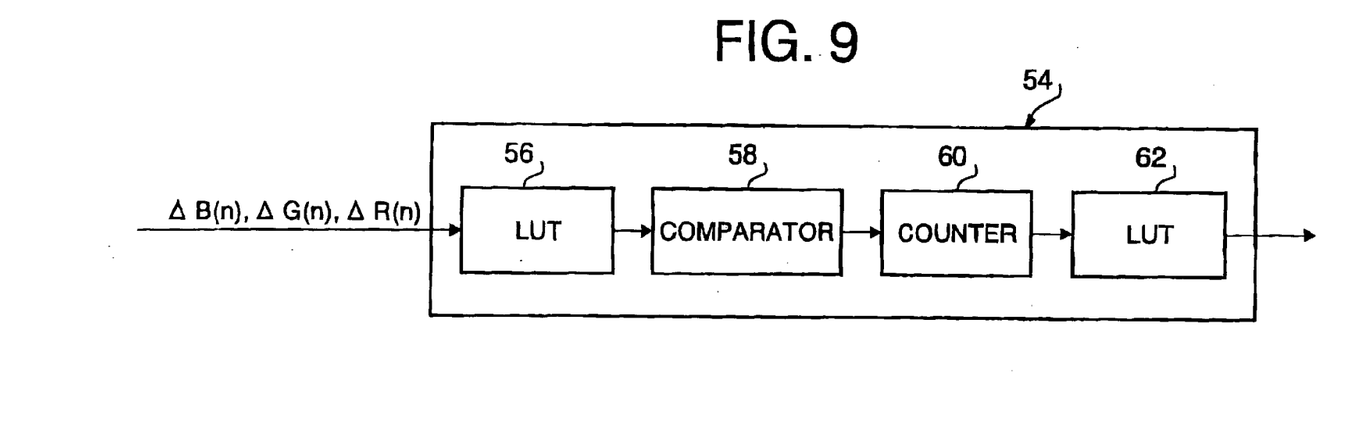
FIG. 9 is a block diagram of a movement detecting circuit 54 of the fifth embodiment.

FIG. 9 is a block diagram of the movement detecting circuit 54. The movement detecting circuit 54 includes a first look-up table (LUT) 56 which is connected with the second adder 50. The second adder 50 provides a digital image signal for each color frame (i.e., for each of pixels 1 to n for each color) as a difference ΔR(n) for each pixel between a current red image signal and a previous red image signal (after noise reduction), a difference ΔG(n) for each pixel 1 to n between a current green image signal and a previous green image signal (after noise reduction), and a difference ΔB(n) for each pixel 1 to n between a current blue image signal and a previous blue image signal (after noise reduction). As an example, in the embodiment, each difference ΔR(n), ΔG(n) and ΔB(n) is eight bit data, and accordingly represents 256 different values (i.e., from 0 to 255) for each pixel 1 to n. If a sign bit is included, the input to the first LUT 56 may take values from −255 to +255. If the absolute value of the input is small, the movement of the object is assumed to be relatively small, and if the absolute value of the input is large, the movement of the object is assumed to be larger.

Figure 10:
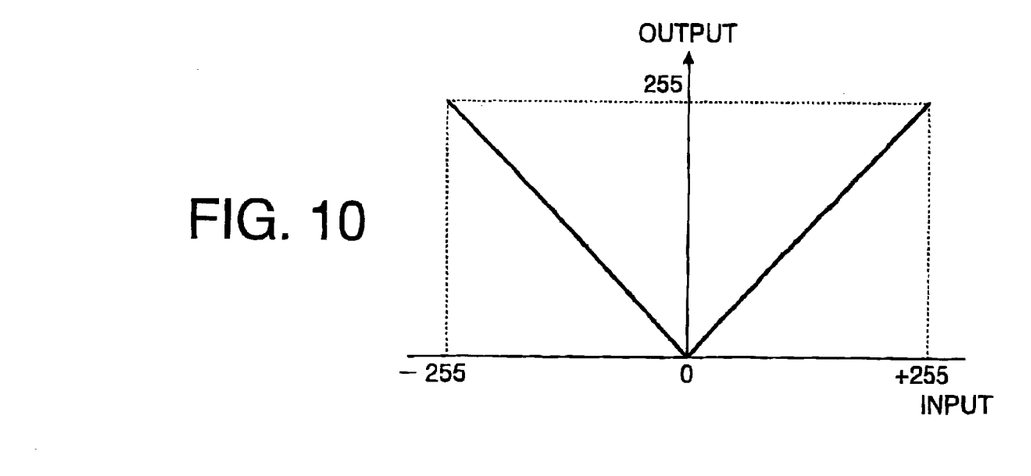
FIG. 10 illustrates a first look-up table.

The first LUT 56 is used to obtain the absolute value of the input thereto. As shown in FIG. 10, the first LUT 56 outputs the absolute value of the input, for example when either of +255 and −255 is input, +255 is output.

A comparator 58 receives the output of the first LUT 56. The comparator 58 compares the output value of the first LUT 56 with a predetermined threshold value, and outputs a logical high (or "1") or logical low (or "0") signal based on the result. The threshold value is, for example, 128, such that if the input is 128 or greater, the comparator 58 outputs "1", and if the input is less than 128, the comparator 58 outputs "0". In other words, the comparator binarizes the input data based on the threshold value.

The output signal of the comparator 58 is input to a counter 60. The counter 60 counts the number of "1"'s output by the comparator 58 for each color frame (i.e., for pixels 1 to n of the single color), outputs the total number of "1"'s to a second LUT 62 after each color frame, and is then reset. The number of "1"'s output by the counter 60 corresponds to the movement of the object, that is, the greater the total number of "1"'s, the greater the amount of object movement.

The second LUT 62 outputs a coefficient α to the first multiplier 40 in accordance with the number input from the counter 60.

It should be noted that the first LUT 56 is not limited to one illustrated in FIG. 10, and various modifications can be used depending on the endoscope system.

Figure 11:
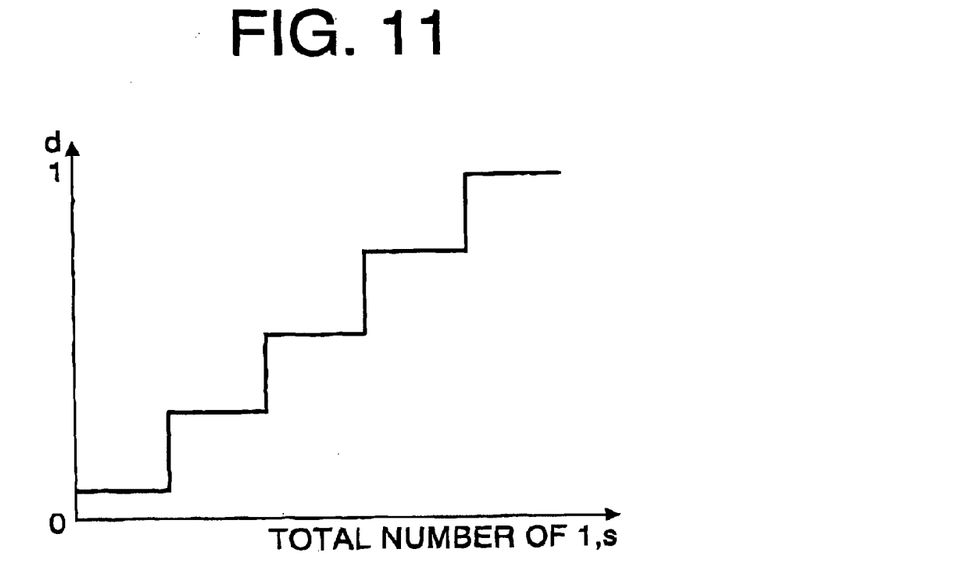
FIG. 11 illustrates a second look-up table.

FIG. 11 shows an example of the relationship between the number of "1"'s output by the counter 60 and the coefficient α output by the LUT 62.

According to FIG. 11, for larger outputs from the counter 60, the coefficient α increases stepwise. Accordingly, if the moving amount of the object is small, the random noise is reduced to a large extent, and, if the moving amount is relatively great, the amount of random noise is reduced as much as possible while also reducing the chance of producing an incidental image.

In FIG. 11, the coefficient α changes stepwise as the output of the counter increases, however, the coefficient α may have some other relationship to the output of the counter 60, such as a proportional relationship or some other predetermined function of the output of the counter 60.

Figure 12:
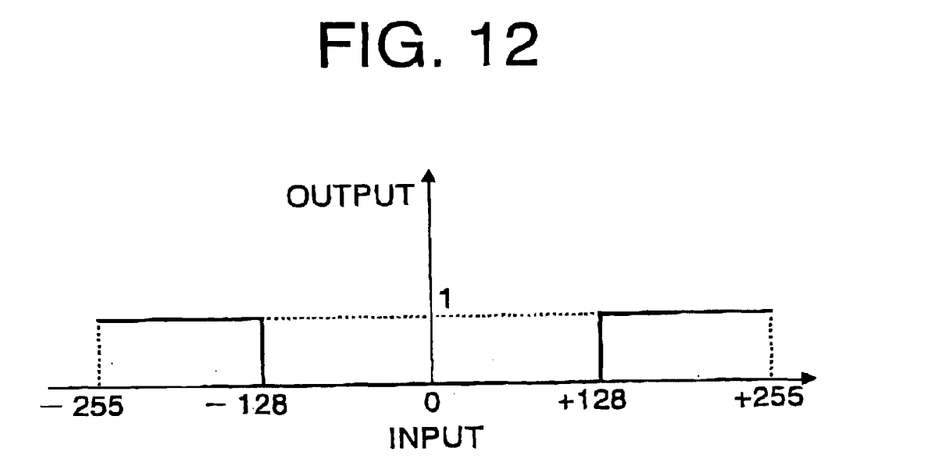
FIG. 12 illustrates an alternative arrangement of the first look-up tables.

FIG. 12 shows an example of a first LUT 56' that may be used as an alternative. The first LUT 56' functions to convert an input value into an absolute value and simultaneously binarize the absolute value. Thus, the first LUT 56' may be used in place of both the first LUT 56 and the comparator 58 shown in FIG. 9. As shown in FIG. 12, when the input value is −128 or lower, a "1" is output, when the input value is greater than −128 and less than +128, a "0" is output, and when the input value is +128 or greater, a "1" is output.

In the above-described embodiments, the filter 18 is provided with segments having the primary colors of red, green and blue, however, alternatively segments having yellow, magenta and cyan can also be used.

According to the embodiments, random noise is effectively reduced, and accordingly, even if the image displayed on the display 38 is observed for a relatively long period, eye-strain is reduced, which enables more accurate diagnosis. Further, even if the object is moving, random noise can be effectively reduced without deteriorating the displayed image.

The present disclosure relates to subject matter contained in Japanese Patent Application No. HEI 08-106184, filed on Apr. 3, 1996, which is expressly incorporated herein by reference in its entirety.

What is claimed is:

1. An electronic endoscope system, comprising:
   an image capturing system, which receives sequential frames of an optical image of an object and sequentially outputs a plurality of image signals respectively corresponding to a plurality of color components of said sequential frames of said optical image;
   a frame memory for storing image signals;
   a noise reduction system, which reduces random noise included in each of said plurality of image signals by combining a non-noise-reduced image signal previously stored in said frame memory and including first random noise, with a non-noise-reduced current image signal from said image capturing system and including second random noise, to form a noise-reduced image signal, and outputs a plurality of said noise-reduced image signals, respectively corresponding to said plurality of image signals;
   a memory which receives said plurality of noise-reduced image signals for each of said sequential frames of said optical image; and
   a video signal generating system, which generates a video signal for each of said sequential frames based on said noise-reduced image signals, corresponding to said plurality of color components.

2. The electronic endoscope system according to claim 1, wherein said video signal includes color components signals corresponding to said plurality of color components.

3. The electronic endoscope system according to claim 1, wherein said plurality of color components includes color components of three primary colors.

4. The electronic endoscope system according to claim 1, further comprising a display device which receives said video signal and displays an image of said object.

5. The electronic endoscope system according to claim 1, wherein said image capturing system uses a field sequential color imaging process.

6. The electronic endoscope system according to claim 1, said image capturing system comprising an image receiving element having a plurality of pixels, and wherein said noise reduction system reduces noise based on both a previous image signal and a current image signal from corresponding pixels of said image receiving element.

7. The electronic endoscope system according to claim 6, wherein said noise reduction system adds said previous image signal stored in said frame memory to said current, unstored image signal and then multiplies the sum by ½ to obtain said noise-reduced image signal.

8. The electronic endoscope system according to claim 1, wherein said image capturing system comprises a white light source, a plurality of color filters, a light transmitting member, and a CCD (Charge Coupled Device), wherein, in sequence and for a predetermined period of time, light emitted by said light source passes sequentially through one of said plurality of color filters and is transmitted through said light transmitting member to illuminate said object, and wherein said plurality of color components correspond to said plurality of filters.

9. The electronic endoscope system according to claim 1, wherein said noise reduction system forms said noise-reduced image signal by feeding forward a non-averaged image signal previously stored in said frame memory and including said first random noise, and combining the previously stored non-averaged image signal with a non-averaged current image signal from said image capturing system and including said second random noise, to form said noise-reduced image signal.

10. The electronic endoscope system according to claim 1, wherein said noise reduction system combines said non-noise-reduced image signal previously stored in said frame memory and including first random noise, with said non-noise-reduced current image signal from said image capturing system and including said second random noise, to form said noise-reduced image signal, without first multiplying by coefficient either of said first non-noise-reduced image signal previously stored in said frame memory and including said first random noise or said non-noise-reduced current image signal from said image capturing system and including said second random noise, by:

adding said non-noise-reduced image signal previously stored in said frame memory and including said first random noise, with said non-noise-reduced current image signal from said image capturing system and including said second random noise, and then multiplying by ½, to form said noise-reduced image signal.

11. The electronic endoscope system according to claim 1, wherein said noise reduction system combines said non-noise-reduced image signal previously stored in said frame memory and including first random noise, with said non-noise-reduced current image signal from said image capturing system and including said second random noise, to form said noise-reduced image signal such that said noise-reduced image signal is a sum of said non-noise-reduced image signal previously stored in said frame memory and including first random noise multiplied by a predetermined coefficient and said non-noise-reduced current image signal from said image capturing system and including said second random noise multiplied by said predetermined coefficient.

* * * * *